(12) United States Patent
Schmitt

(10) Patent No.: US 6,851,854 B2
(45) Date of Patent: Feb. 8, 2005

(54) X-RAY APPARATUS WITH INTERCHANGEABLE FILTER AND AREA DOSE MEASURING DEVICE

(75) Inventor: Thomas Schmitt, Forchheim (DE)

(73) Assignee: Siemens Aktiengesellschaft, Münich (DE)

(*) Notice: Subject to any disclaimer, the term of this patent is extended or adjusted under 35 U.S.C. 154(b) by 91 days.

(21) Appl. No.: 10/346,861

(22) Filed: Jan. 17, 2003

(65) Prior Publication Data

US 2003/0138079 A1 Jul. 24, 2003

(30) Foreign Application Priority Data

Jan. 18, 2002 (DE) .......................................... 102 01 868

(51) Int. Cl.[7] .......................... G01D 18/00; G21K 3/00
(52) U.S. Cl. ....................... 378/207; 378/108; 378/156; 378/157; 250/252.1
(58) Field of Search .......................... 378/97, 98.7, 108, 378/156, 157, 158, 159, 207; 250/252.1, 374, 382, 389

(56) References Cited

U.S. PATENT DOCUMENTS

| | | | | |
|---|---|---|---|---|
| 4,051,377 A | * | 9/1977 | Kemner et al. ............... 378/16 |
| 5,019,713 A | * | 5/1991 | Schmidt ................... 250/492.3 |
| 5,396,889 A | * | 3/1995 | Ueda et al. .................. 600/407 |
| 5,619,042 A | * | 4/1997 | Hughes .................... 250/492.3 |
| 5,648,765 A | * | 7/1997 | Cresap et al. ............... 340/10.4 |
| 6,036,362 A | | 3/2000 | Schmitt ....................... 378/206 |
| 6,292,537 B1 | * | 9/2001 | Zimmermann .............. 378/108 |

FOREIGN PATENT DOCUMENTS

| | | |
|---|---|---|
| DE | 83 12 137 | 9/1993 |
| DE | 198 32 973 | 1/2000 |
| DE | 33 12 137.4 | 9/2003 |

* cited by examiner

Primary Examiner—Allen C. Ho
(74) Attorney, Agent, or Firm—Schiff Hardin LLP

(57) ABSTRACT

An X-ray apparatus has a radiation source, an interchangeable radiation filter and an area dose measuring device having a measurement chamber with an allocated evaluation device for determining the area dose product on the basis of a measured signal provided by the measurement chamber. The measurement chamber is arranged preceding the filter in the beam path with reference to the radiation propagation direction. A detector recognizes the nature and/or the type of radiation filter that is currently inserted in the beam path. The evaluation device corrects the area dose product that is calculated from the measured signal from the measurement chamber on the basis of at least one filter-specific correction value that is selected as a result of the detection of the filter nature and/or type.

21 Claims, 2 Drawing Sheets

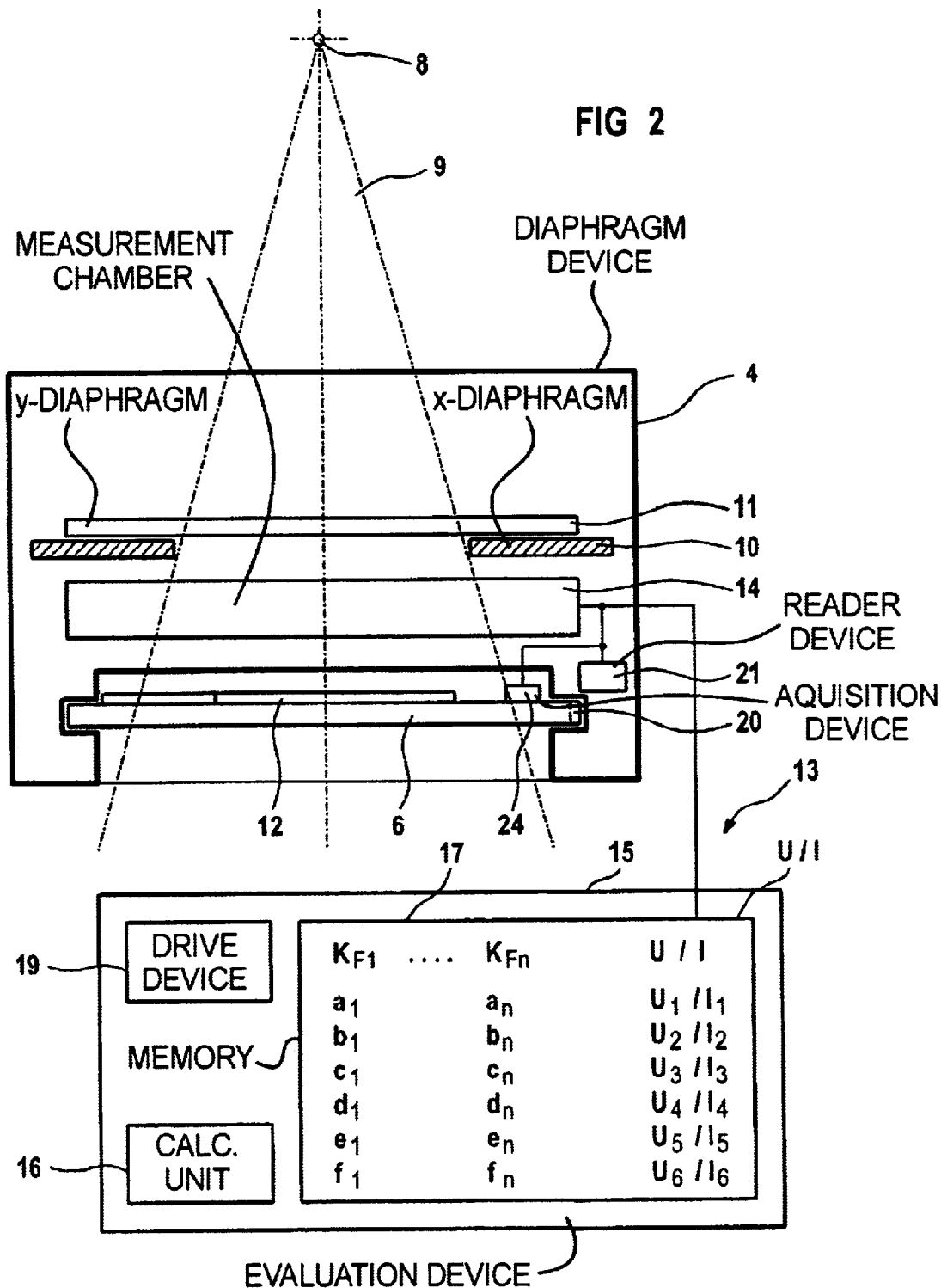

X-RAY APPARATUS WITH INTERCHANGEABLE FILTER AND AREA DOSE MEASURING DEVICE

BACKGROUND OF THE INVENTION

1. Field of the Invention

The present invention is directed to an X-ray apparatus of the type having a radiation source, an interchangeable radiation filter and an area dose measuring device with a measurement chamber and an allocated evaluation device for determining the area dose product on the basis of the measured signals provided by the measurement chamber, with the measurement chamber arranged preceding the filter in the beam path with reference to the radiation propagation direction.

2. Description of the Prior Art

Measurement of the area dose product allows determination of the amount of X-radiation applied to the examination subject, for example a patient. This measurement is conventionally undertaken with an area dose-measuring device having a measurement chamber that is arranged in the beam path. This measurement chamber usually is an ionization chamber through which the X-rays pass and at which an output signal dependent on the amount of radiation can be obtained. The applied, surface area-dependent dose can be determined from this signal, usually in $\mu Gym^2$ units.

Radiation filters are often employed in known X-ray apparatuses in order to attenuate or entirely blank the X-rays in certain filter-specific ranges. A large variety of interchangeable and employable filters are known, for example shoulder filters, foot filters, pelvis filters or skull filters. These filters, that are usually fashioned in the form of essentially rectangular plates, are inserted into the beam path. These insertion guides usually are arranged outside the housing containing the measurement device and further parts of the area dose-measuring device, such as, the evaluation device. The measurement chamber lies in front of the filter with reference to the radiation propagation direction. The measurement chamber often is integrated into a diaphragm device that follows the radiation source in the propagation direction, particularly in the depth diaphragm, and which has an outer housing section at which the insertion guides for the plate-like radiation filters are located.

Due to this arrangement wherein the radiation filters follow the measurement chamber, the problem arises that the filter effect does not enter into the determination of the area dose product. The filter performance that attenuates the X-rays that are actually applied to the subject is not taken into consideration since the measurement occurs preceding the radiation filter. Ultimately, thus, the applied dose is lower than that indicated by the "unfiltered" measured result.

SUMMARY OF THE INVENTION

An object of the present invention is to provide an X-ray apparatus that eliminates the aforementioned disadvantage associated with known X-ray apparatus in the determination of the area dose.

This object is achieved in accordance with the invention in an X-ray apparatus of the type initially described having a detector for recognizing a filter characteristic of the filter currently in use, such as the nature and/or the type of filter, and an evaluation fashioned for correcting the calculated surface dose product on the basis of at least one filter-specific correction value dependent on the identification of the filter in use.

In the inventive X-ray apparatus, the detector makes it possible to determine what filter type or what kind of filter is inserted into the beam path following the measurement chamber. On the basis of this knowledge, which is forwarded to the evaluation device, the evaluation device is able to suitably correct the area dose product that is calculated in the evaluation device based on the signal acquired by the measurement chamber preceding the radiation filter. This correction is undertaken using at least one filter-specific correction value, i.e. a correction value that takes the filter properties of the recognized filter into consideration. As a result, it is possible to calculate the filter effect of the following radiation filter and to include this in the calculated area dose product. This product thus indicates the actually applied X-rays as accurately as possible, rather than the unattenuated amount of radiation.

In order to recognize the nature or type of filter, it is necessary to be able to identify each inserted or insertable filter so that its filter-specific features or characteristics can be likewise identified. In a first embodiment of the invention, the detector for recognizing the nature and/or type of filter can be a transponder arranged at the filter and an acquisition device that picks up the transponder signal. This acquisition device, which can also be the corresponding excitation device, activates the transponder to emit the transponder signal. The acquisition device can be external to the surface dose-measuring device or the evaluation device itself can be fashioned for this purpose. Each radiation filter has its own filter-specific transponder, so that a simple acquisition and discrimination are possible.

As an alternative, the detector for recognizing the nature and/or type of filter can include at least one identification specifying the nature and/or type of filter and an acquisition device that acquires the identification. Expediently, the identification is a coding. According to a first alternative of the invention, this can be an electronic coding that can be interrogated via the acquisition device. For example, the evaluation device itself also can be employed as the acquisition device. Each radiation filter can have a small integrated chip associated therewith that, for example, is automatically contacted by a corresponding connector plug upon insertion of the filter, the connection to the acquisition device being closed through the chip/plug connection.

As an alternative, the identification can be acquired by an optical reader device. For example, a label or an imprint can be used, particularly a bar code or the like. Further, specific reflection patterns at the filter can be employed as the identification, these being acquired via the optical reader device. Another alternative is to provide the identification as a structure applied to the radiation filter, particularly in the form of notches or the like. This structure likewise can be acquired by the optical reader device.

A further alternative for fashioning the identification in accordance with the invention is to provide projections or depressions, for example in the form of notches, at the radiation filter which activate switch or sensor elements when the radiation filter is introduced. The projections or depressions are specifically fashioned for each radiation filter, so that a specific switch or sensor element actuation occurs for each radiation filter. The respective filter type or kind of filter can then be recognized from the combination of actuated switch or sensor elements.

Magnetic identifications also can be used that, for example, can be acquired via Hall sensors that detect the generated magnetic field. For example, a number of magnetic identifications can be filter-specifically arranged here along a side of the filter, the positioning or the magnetic fields of these identifications in turn representing a coding for the filter type and/or kind of filter. Dependent on the output signals of the Hall sensor or sensors, the kind of filter or the filter type can be identified.

As already described, it is expedient to integrate the surface dose measuring device in a diaphragm device that follows the radiation source, particularly in the depth diaphragm, so that an overall closed system is achieved. The evaluation device also can be integrated; however, it is also possible to externally position the evaluation device.

Although a specific correction value can be allocated to each radiation filter which always is utilized for correction given employment of that radiation filter, it is expedient for the correction value employed for correction to be dependent on at least one parameter representing a criterion for the generated X-rays. The applied X-rays are variable within broad ranges by means of a corresponding setting of the operating parameters, i.e., for example, the operating voltage or the operating current. In order to be able to design the correction of the area dose product even more exactly, it is expedient to employ a correction value that is adapted to the employed parameters that influence the X-rays. For example, a number of correction values can be stored in the evaluation device that are allocated or dependent on specific parameters that influence the X-rays such as, for example, the tube voltage or the tube current. Dependent on which operating parameters are set by the physician or the radiology technician, the evaluation device that has the corresponding operating parameter information available to it then selects the appropriate correction value from the stored, filter-specific family of correction values. The resulting thus takes the actual operating conditions into consideration.

DESCRIPTION OF THE DRAWINGS

FIG. 2 is a schematic illustration of the relevant parts of the inventive surface dose measuring device.

DESCRIPTION OF THE PREFERRED EMBODIMENTS

Figure 1:
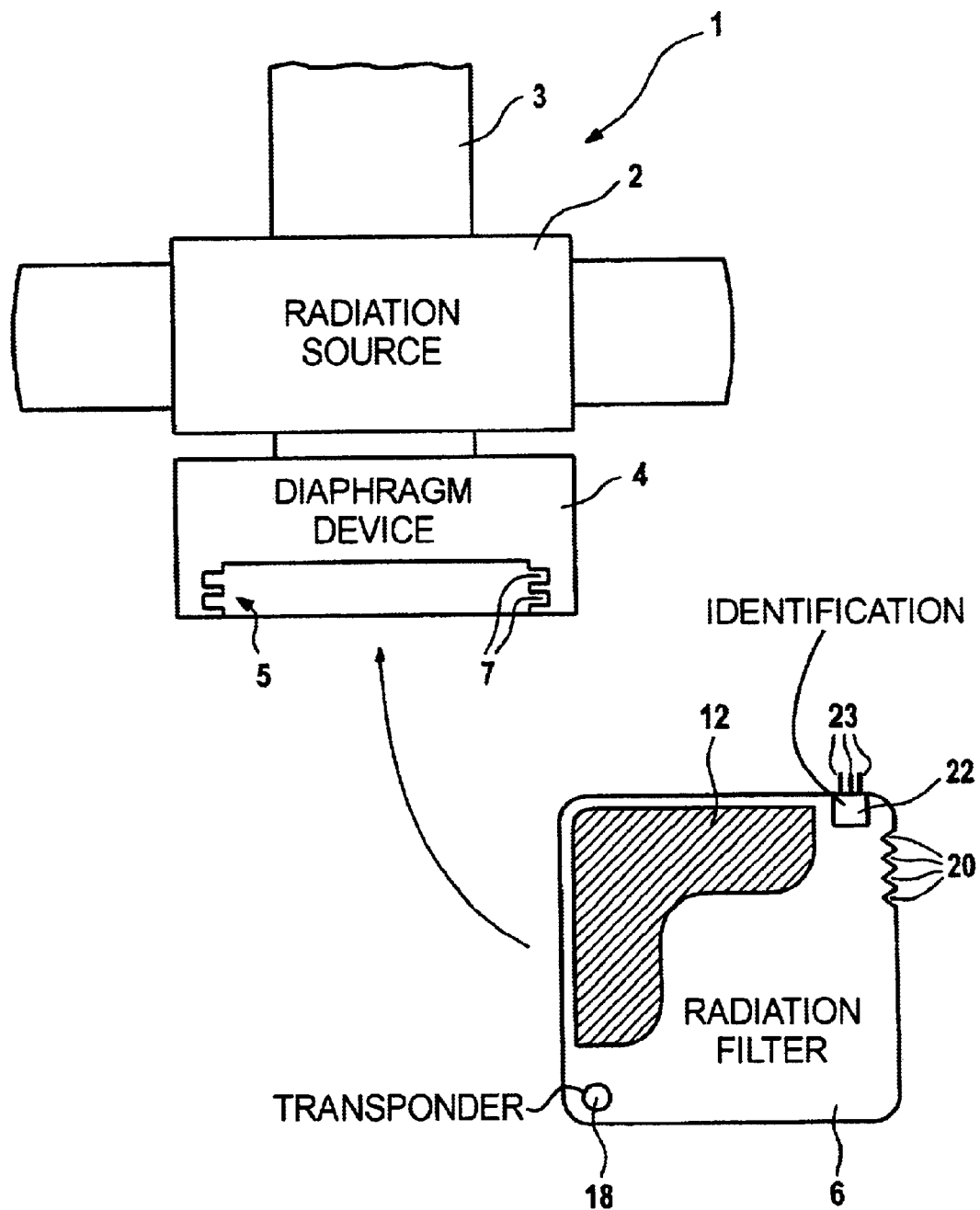
FIG. 1 is a schematic illustration of an inventive X-ray apparatus as well as a releasably introducible radiation filter.

FIG. 1 shows an inventive X-ray apparatus 1, with only the radiation source 2 being shown, this being arranged at a telescoping arm 3 of a ceiling-mounted stand (not shown in detail). A diaphragm device 4, for example a depth diaphragm, is provided under the radiation source 2 in the illustrated example; the shape of the beam in the x-direction and y-direction, or in the plane defined by those directions, can be shaped by this diaphragm device 4, which shall be discussed in brief below.

At its housing, the depth diaphragm 4 has receptacles 5 for the acceptance of one or more radiation filters 6. In the illustrated example, the receptacles are fashioned as lateral insertion channels 7 into which an essentially rectangular, plate-shaped radiation filter 6 is inserted. As shown in FIG. 2, the inserted filter 6 is then located in the beam path of the X-rays generated by the radiation source 2, which is not shown in detail in FIG. 2. Only the focus 8 of the radiation source 2 is shown, the X-ray beam 9 expanding as it proceeds from said focus 8. The shape of the X-ray beam is defined by x and y diaphragms 10, 11. The X-ray beam 9 likewise passes through the radiation filter 6, so it is attenuated in the regions wherein the radiation filter 6 includes an X-ray filter medium 12.

In order to determine the area dose product, an area dose measuring device 13 is provided that has a measurement chamber 14, such as an ionization chamber, that is arranged in the beam path and precedes the radiation filter 6, and also has an evaluation device 15 that is external therefrom in the illustrated example. The X-rays penetrate into the ionization chamber 14, which leads to a particle ionization dependent on the radiation dose and ultimately leads to an output signal that is dependent on the degree of ionization. The functioning of such an ionization chamber as well as the calculation of the area dose product dependent on the output signal are well-known. The calculation ensues in the evaluation device 15 that receives the output signal of the ionization chamber 14. A suitable calculating unit 16 is provided for the calculation. As warranted, a partial system control can ensue via the evaluation device 15 or the calculating unit 16 when an adequate area dose product is reached, but this shall not be discussed in detail. This is also well-known and need not be presented herein.

The evaluation device 16 also has a memory device 17 available to it wherein a number of filter-specific correction value families $K_{F1} \ldots K_{Fn}$ are stored. A filter-specific correction value for the area dose product exists for each radiation filter 6 that is employed (a large variety of radiation filters can be employed) and the correction of this area dose product is necessary because the measurement chamber 14 is situated in front of the radiation filter 6 and the output signal at the side of the ionization chamber consequently is not influenced by the filter effect, and thus the beam attenuation produced by the radiation filter would not otherwise be taken into consideration.

In order to be able to select the right correction value from the stored correction values, it is necessary to be able to identify the inserted radiation filter 6 in terms of its nature or its type. Suitable means for recognizing the nature or type are provided for this purpose. First, a unique identification of each radiation filter 6 is required. The radiation filter 6 shown in FIG. 1 shows some identification versions. A transponder 18 can be used, with each radiation filter having its own specific transponder 18. For example, a suitable drive device 19 can be provided in the evaluation device 15, for driving the transponder 18 such that it transmits its transponder signal, which is in turn received and interpreted by the drive device 19 and the corresponding filter can be recognized in this way. Each filter has its own transponder that emits a filter-specific transponder signal, so that a definitive discrimination and recognition is possible.

A further, alternative identification version is a number of specifically shaped indentations 20 at the edge of the radiation filter 6 that, for example, can be acquired via an optical device 21 that is integrated in the diaphragm device 4. The identification and coding of the respective filter type ensues by means of the shape of the employed indentations 20 and their arrangement and positioning relative to one another. Arbitrary codings are possible in this version.

Alternatively, reflection fields can be applied to the filter 6 that are acquired via the optical read device 21.

Another possibility shown in FIG. 1 is the employment of an electronic identification 22, for example in the form of a small microchip, that is automatically coupled via its terminal pins 23 to a suitable acquisition device 24 in the diaphragm, that then emits a corresponding output signal that is forwarded to the evaluation device 15. Only one identification version need be provided at a radiation filter 6; the employment of the three different identification possibilities in FIG. 2 is only for explaining a number of exemplary alternatives. The same is true of the employment of the detector for the recognition of the identification. Only one of the drive device 19, the optical reader device 21 or the electronic reader device 24 is to be provided.

In any case, the evaluation device 15 receives an information signal that describes the filter type or the kind of filter. In addition, the evaluation device 15 is provided with information data about the operating parameters of tube voltage U and tube current I that have been set for generating the X-rays. In addition to the information about the filter being utilized, these serve the purpose of selecting the correct filter-specific correction for the inserted filter value from the family of correction values.

Two correction value families for two specific radiation filters, namely the filters F1 and Fn, are shown as an example in the memory area 17 in FIG. 2. The respective correction values in the two families are $a_1, b_1 \ldots f_1$ and $b_n \ldots f_n$, whereby the index 1 indicates the correction value family for the filter F1 and the index n indicates the correction value family for the filter Fn.

Further, respective operating parameters U/I are indicated, namely $U_1/I_1, U_2/I_2, \ldots, U_6/I_6$.

The respective correction value family $K_{F1} \ldots K_{Fn}$ is selected on the basis of the pending information signal about the introduced filter. Let it be assumed that the radiation filter F1 is introduced, so that one of the correction values $a_1, \ldots f_1$ will thus be employed for the correction.

The exact determination of the correction value to be employed ensues on the basis of the pending voltage and current signals. Let it be assumed that the voltage and the current lie in respective value ranges around $U_3$ and $I_3$. In this case, thus, the correction value $c_1$ would be utilized for the correction of the originally calculated area dose product without taking the filter attenuation into consideration. For example, the correction value c1 can be a defined value, for example in a $\mu Gym^2$ unit, that is subtracted from the calculated area dose product. Alternatively, it can be a suitable percentage by which the calculated area dose product is to be reduced, etc. Different forms of correction values are employed as appropriate. When the pending voltage and current values do not lie in a prescribed interval range, i.e. when, for example, they are not to be allocated to $U_4$ and $I_4$ but, for example, to $U_2$ and $I_5$, it is also possible to make a defined selection for determining the specific correction value, so that, for example, $c_1$ is selected given such a combination. Alternatively, there is the possibility of calculating, for example, an average value from $b_1$ and $e_1$ (with respect to $U_2$ or $I_5$). Different approaches are also possible.

The area dose product calculated in this way is then, for example, either output by the calculating device 16 and displayed at a monitor, or is forwarded to a central control device, which takes the area dose product into consideration in the framework of the higher-ranking control of the calculating device 16.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray apparatus comprising:
   a radiation source which emits a radiation beam propagating along a propagation direction;
   at least one radiation filter insertable into said radiation beam, said radiation filter having a filter effect which alters said radiation beam;
   an area dose measuring device having a measurement chamber which emits measured signals by interacting with said radiation beam, and an evaluation device, at least said measurement chamber being disposed preceding said filter in said propagation direction;
   a recognition unit for interacting with said radiation filter when said radiation filter is disposed in said radiation beam to identify said radiation filter and which provides an identification signal to said evaluation device; and
   said evaluation device calculating an area dose product of said radiation beam dependent on said measured signals and correcting said area dose product with at least one filter-specific correction value dependent on the filter effect of the radiation filter identified by said recognition unit.

2. An X-ray apparatus as claimed in claim 1 wherein said recognition unit identifies the nature of said radiation filter.

3. An X-ray apparatus as claimed in claim 1 wherein said recognition unit identifies a type of said radiation filter.

4. An X-ray apparatus as claimed in claim 1 wherein said recognition unit comprises a transponder disposed at said radiation filter, which emits a transponder signal, and an acquisition device which receives said transponder signal.

5. An X-ray apparatus as claimed in claim 1 wherein said recognition unit comprises an identification on said radiation filter from which said filter effect is determined, and a detector for detecting said identification.

6. An X-ray apparatus as claimed in claim 5 wherein said identification comprises a coding.

7. An X-ray apparatus as claimed in claim 5 wherein said identification comprises an electronic identification which is interrogated by said detector.

8. An X-ray apparatus as claimed in claim 5 wherein said identification is an electronic identification that is read out by said detector.

9. An X-ray apparatus as claimed in claim 5 wherein said identification comprises optically detectable indicia, and wherein said detector is an optical reader.

10. An X-ray apparatus as claimed in claim 9 wherein said optical indicia comprise a bar code.

11. An X-ray apparatus as claimed in claim 9 Wherein said identification comprises a label carrying said indicia.

12. An X-ray apparatus as claimed in claim 9 wherein said identification comprises an imprint on said radiation filter comprising said indicia.

13. An X-ray apparatus as claimed in claim 9 wherein said indicia are formed by a physical structure of said radiation filter.

14. An X-ray apparatus as claimed in claim 13 wherein said physical structure comprises notches.

15. An X-ray apparatus as claimed in claim 5 wherein said identification comprises a surface alteration of said radiation filter selected from the group consisting of projections and indentations, and wherein said detector is selected from the group consisting of switches and sensor elements actuated by said surface alteration.

16. An X-ray apparatus as claimed in claim 5 wherein said identification comprises a magnetic identification and wherein said detector is a magnetic field detector.

17. An X-ray apparatus as claimed in claim 1 further comprising a diaphragm device in which said at least one radiation filter is receivable, and wherein at least said measuring chamber is integrated in said diaphragm device.

18. An X-ray apparatus as claimed in claim 17 wherein said diaphragm device is a depth diaphragm.

19. An X-ray apparatus as claimed in claim 1 wherein said radiation source emits said radiation beam dependent on at least one parameter which influences said radiation beam, and wherein said evaluation device selects said correction value dependent on said at least one parameter.

20. An X-ray apparatus as claimed in claim 19 wherein said radiation source is an x-ray source, and wherein said parameter is selected from the group consisting of operating voltage of said X-ray source and operating current of said x-ray source.

21. An X-ray apparatus as claimed in claim 19 comprising a memory accessible by said evaluation device in which, for said at least one radiation filter, a family of correction values are stored, the correction values in said family being respectively dependent on different values of said at least one operating parameter.

* * * * *